(12) United States Patent
Kawano

(10) Patent No.: US 7,239,384 B2
(45) Date of Patent: Jul. 3, 2007

(54) LASER-SCANNING FLUOROSCOPY APPARATUS

(75) Inventor: Yoshihiro Kawano, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/209,693

(22) Filed: Aug. 24, 2005

(65) Prior Publication Data

US 2006/0044556 A1  Mar. 2, 2006

(30) Foreign Application Priority Data

Aug. 27, 2004  (JP) .............................. 2004-248719

(51) Int. Cl.
*G01J 3/30* (2006.01)
(52) U.S. Cl. .................................... 356/317
(58) Field of Classification Search ...................... None
See application file for complete search history.

(56) References Cited

U.S. PATENT DOCUMENTS 5,751,417 A  5/1998  Uhl
6,344,653 B1 *  2/2002  Webb et al. ............. 250/458.1
6,522,403 B2 *  2/2003  Wilson et al. ............... 356/328
7,046,360 B2 *  5/2006  Fujimoto et al. ........... 356/326

FOREIGN PATENT DOCUMENTS

JP    9-502269    4/1997
JP    2001-272275    10/2001

* cited by examiner

*Primary Examiner*—Tu T. Nguyen
(74) *Attorney, Agent, or Firm*—Kenyon & Kenyon LLP

(57) ABSTRACT

A laser-scanning fluoroscopy apparatus includes a laser light source of a plurality of wavelengths; a spectroscopic device for splitting laser beams according to wavelength; a focusing lens for focusing the split laser beams; a wavelength-selecting reflection device which includes a plurality of reflection sections disposed near the focal positions, spaced out at predetermined intervals in a split direction to reflect the laser beams with different wavelengths and a transmission section arranged adjacent to the reflection sections; a diffraction grating for combining the reflected laser beams; a scanning section for two-dimensionally scanning the combined laser beams; an objective optical system for focusing the scanned laser beams onto a tissue; and a photodetector for detecting fluorescence emitted from the tissue.

2 Claims, 10 Drawing Sheets

LASER-SCANNING FLUOROSCOPY APPARATUS

BACKGROUND OF THE INVENTION

1. Field of the Invention

The present invention relates to laser-scanning fluoroscopy apparatuses.

2. Description of Related Art

In a fluoroscopy apparatus for emitting excitation light onto a tissue to examine fluorescence generated by the tissue, it is necessary to separate fluorescence from excitation light to detect the fluorescence. A dichroic mirror is normally used in known methods for separating fluorescence from excitation light. However, since the wavelength of excitation light entering the tissue is close to that of fluorescence generated by that excitation light, it is often difficult to design a dichroic mirror that can efficiently separate fluorescence from excitation light.

In order to overcome this difficulty, a method for separating fluorescence from excitation light using a spectroscopic device, such as a prism, is proposed (see, for example, U.S. Pat. No. 5,751,417, PCT Japanese Translation Patent Publication No. Hei-9-502269, and Japanese Unexamined Patent Application Publication No. 2001-272275).

U.S. Pat. No. 5,751,417 discloses a confocal fluorescence microscope apparatus that does not use a dichroic mirror. This confocal fluorescence microscope apparatus includes an aperture for converting light emitted from a light source into a plurality of light strips; a prism; and a mirror for selectively reflecting part of each light strip split by the prism to separate fluorescence returning from a tissue and excitation light by causing the fluorescence to pass through a slit provided at the mirror, thus allowing a photodetector to detect the separated fluorescence.

PCT Japanese Translation Patent Publication No. Hei-9-502269 discloses an apparatus for selectively detecting light with at least two spectral bands in a beam using a prism and a mirror having an aperture. Japanese Unexamined Patent Application Publication No. 2001-272275 discloses an apparatus for selectively detecting at least one spectral region of a beam in the beam path of a confocal scanning microscope using a prism and a triangular mirror.

Although the confocal fluorescence microscope described in U.S. Pat. No. 5,751,417 can separate fluorescence from excitation light without a dichroic mirror, it cannot detect a plurality of fluorescence beams generated by simultaneously emitting a plurality of excitation light beams. In other words, although the confocal fluorescence microscope described in U.S. Pat. No. 5,751,417 can change the wavelength of excitation light and the wavelength of fluorescence to be passed through the slit by mirror reflection by moving the mirror in a direction intersecting with the optical axis, it is difficult to simultaneously emit excitation light with a plurality of wavelengths and to simultaneously detect fluorescence with a plurality of wavelengths.

Furthermore, although the apparatuses described in PCT Japanese Translation Patent Publication No. Hei-9-502269 and Japanese Unexamined Patent Application Publication No. 2001-272275 can selectively detect light with a plurality of wavelengths, these apparatuses require a plurality of apertures and a plurality of triangular mirrors to be arranged at certain intervals. This is disadvantageous in that the structures become complicated and the sizes of the apparatuses increase. In addition, a plurality of apertures and triangular mirrors need to be adjusted individually, making it difficult to detect light with high accuracy due to this adjustment procedure.

BRIEF SUMMARY OF THE INVENTION

The present invention has been conceived in light of these circumstances, and it is an object of the present invention to provide a laser-scanning fluoroscopy apparatus for allowing fluorescence generated by a tissue to be efficiently detected and for simultaneously emitting excitation light with a plurality of wavelengths to simultaneously detect fluorescence with a plurality of wavelengths.

In order to achieve the above-described objects, the present invention provides the following solutions.

In one aspect, the present invention provides a laser-scanning fluoroscopy apparatus including: a laser light source for emitting laser beams with a plurality of wavelengths; a spectroscopic device for splitting the laser beams emitted from the laser light source according to wavelength; a focusing lens for focusing the laser beams split by the spectroscopic device; and a wavelength-selecting reflection device. The wavelength-selecting reflection device includes a plurality of reflection sections, disposed near focal positions of the focusing lens, spaced out at predetermined intervals in a split direction of the spectroscopic device to reflect the laser beams with different wavelengths and a transmission section arranged adjacent to the reflection sections. The laser-scanning fluoroscopy apparatus further includes: a diffraction grating for combining the laser beams reflected by the wavelength-selecting reflection device; a scanning section for two-dimensionally scanning the laser beams combined by the diffraction grating; an objective optical system for focusing the laser beams scanned by the scanning section onto a tissue; and a photodetector for detecting fluorescence emitted from the tissue, the fluorescence returning through the objective optical system, the scanning section, and the diffraction grating, and passing through the transmission section of the wavelength-selecting reflection device. A width dimension, as measured along the split direction, of each reflection section of the wavelength-selecting reflection device is smaller than a width dimension of the transmission section.

According to the present invention, laser beams emitted from the laser light source are split according to wavelength by the spectroscopic device and are focused onto focal positions by the focusing lens. Since the laser beams have a narrow spectral band, the split laser beams are converted into thin strips of light with a small width and are incident upon the wavelength-selecting reflection device. Since the wavelength-selecting reflection device includes reflection sections arranged near the focal positions of the focusing lens, the focused strips of laser light are easily reflected by the reflection sections. The laser beams are combined by the diffraction grating, scanned two-dimensionally by the scanning section, and emitted onto the tissue through the objective optical system.

In the tissue irradiated with the laser beams, fluorescence is emitted when a fluorescent material is excited. The emitted fluorescence returns along the same light path through the objective optical system, the scanning section, and the diffraction grating. Since the fluorescence has a wavelength different from those of the laser beams, it is deflected in a slightly different direction in the diffraction grating and is incident upon the wavelength-selecting reflection device. Since the reflection sections of the wavelength-selecting reflection device are formed to be narrower than the transmission section, the fluorescence easily passes through the transmission section and is efficiently detected by the photodetector.

Furthermore, since the reflection sections are spaced out at intervals in the split direction of the spectroscopic device to reflect the laser beams with different wavelengths, laser beams with a plurality of wavelength can be simultaneously radiated to the tissue. Since the fluorescence returning from the tissue is incident upon the wavelength-selecting reflection device at a position slightly shifted from the reflection sections, the fluorescence emitted in response to all laser beams easily passes through the transmission section and is efficiently detected by the photodetector.

In the above-described aspect of the invention, it is preferable that the wavelength-selecting reflection device be formed of a transparent substrate coated with strips of reflection films. On the transparent substrate, the reflection films can be formed in thin strips and can thus be arranged with high accuracy. The laser beams are reflected by the reflection sections formed of the reflection films, and the fluorescence passes through the transparent substrate between the reflection films. Since the transmittance of the transparent substrate can be increased more easily than the reflectivity of the reflection films is increased, fluorescence with less light intensity can be detected by the photodetector without loss.

In the above-described aspect of the invention, the wavelength-selecting reflection device may include a plurality of areas having the reflection sections at different positions and a switching device for selecting the areas.

When the areas are selected by the operation of the switching device, at least one of the plurality of laser beams emitted from the laser light source can be selectively reflected onto the tissue.

In the above-described aspect of the invention, the spectroscopic device may include an acoustooptic element.

According to the acoustooptic element, since the angles of the emitted laser beams can easily be changed merely by changing the input frequency, the emitted laser beams can be finely adjusted to be accurately aligned with the reflection sections.

In the above-described aspect of the invention, it is preferable that a conditional expression 100:25<H1:H2<400:1 be satisfied, where H1 is a width dimension corresponding to a splittable spectral band in the wavelength-selecting reflection device, H2 is a width dimension of each reflection section, and H1:H2 represents the ratio of H1 to H2.

Furthermore, in a second aspect, the present invention provides a laser-scanning fluoroscopy apparatus including: a laser light source for emitting laser beams with a plurality of wavelengths; a spectroscopic device for splitting the laser beams emitted from the laser light source according to wavelength; a focusing lens for focusing the laser beams split by the spectroscopic device; and a mirror device. The mirror device includes a plurality of first reflection sections disposed near focal positions of the focusing lens, spaced out in a split direction of the spectroscopic device to reflect the laser beams with different wavelengths in a first direction and a second reflection section arranged adjacent to the first reflection sections to reflect incident light in a second reflection direction. The laser-scanning fluoroscopy apparatus further includes: a diffraction grating for combining the laser beams reflected by the first reflection sections in the first direction; a scanning section for two-dimensionally scanning the laser beams combined by the diffraction grating; an objective optical system for focusing the laser beams scanned by the scanning section onto a tissue; and a photodetector for detecting fluorescence emitted from the tissue, the fluorescence returning through the objective optical system, the scanning section, and the diffraction grating, and being reflected at the second reflection section of the mirror device. A width dimension, as measured along the split direction, of each first reflection section of the mirror device is smaller than a width dimension of the second reflection section.

According to this aspect of the present invention, when the laser beams emitted from the laser light source are incident upon the mirror device, the laser beams are radiated by the first reflection sections arranged at positions corresponding to respective wavelengths onto the tissue through the diffraction grating, the scanning section, and the objective optical system. Furthermore, the fluorescence emitted from the tissue returns through the objective optical system, the scanning section, and the diffraction grating. Since the fluorescence has a wavelength different from those of the laser beams, it is reflected in a direction different from the directions in which the laser beams are incident. Thus, the fluorescence is not reflected at the first reflection sections but is reflected at the second reflection section neighboring them and is detected by the photodetector arranged in a reflection direction of the second reflection section. In this case, since the first reflection sections of the mirror device are formed to be thinner than the second reflection section, the fluorescence incident upon the mirror device is easily reflected by the second reflection section and is efficiently detected by the photodetector. Therefore, when laser beams with a plurality of wavelengths are simultaneously radiated onto the tissue, fluorescence emitted from the tissue excited by each laser beam can be detected.

In the above-described aspect of the invention, the mirror device may include a plurality of movable mirrors such that the first reflection sections and the second reflection section can be relocated.

For example, just like a digital micro-mirror device (DMD) having a plurality of movable micro-mirrors, the wavelengths of laser beams to be radiated onto the tissue can be freely selected by arbitrarily switching among patterns composed of the first reflection sections and the second reflection section.

According to the present invention, since a plurality of laser beams generated by the laser light source are split by the spectroscopic device to be formed in thin strips, fluorescence emitted from the tissue can pass through the large transmission section that can transmit substantially 100% of fluorescence for efficient detection. Furthermore, fluorescence resulting from laser beams with a plurality of wavelengths simultaneously radiated onto the tissue can be guided to the light detection section through the large transmission section without loss. This is advantageous in terms of efficient detection of the fluorescence.

DETAILED DESCRIPTION OF THE INVENTION

A laser-scanning fluoroscopy apparatus according to a first embodiment of the present invention will now be described with reference to FIGS. 1 to 3.

Figure 1:
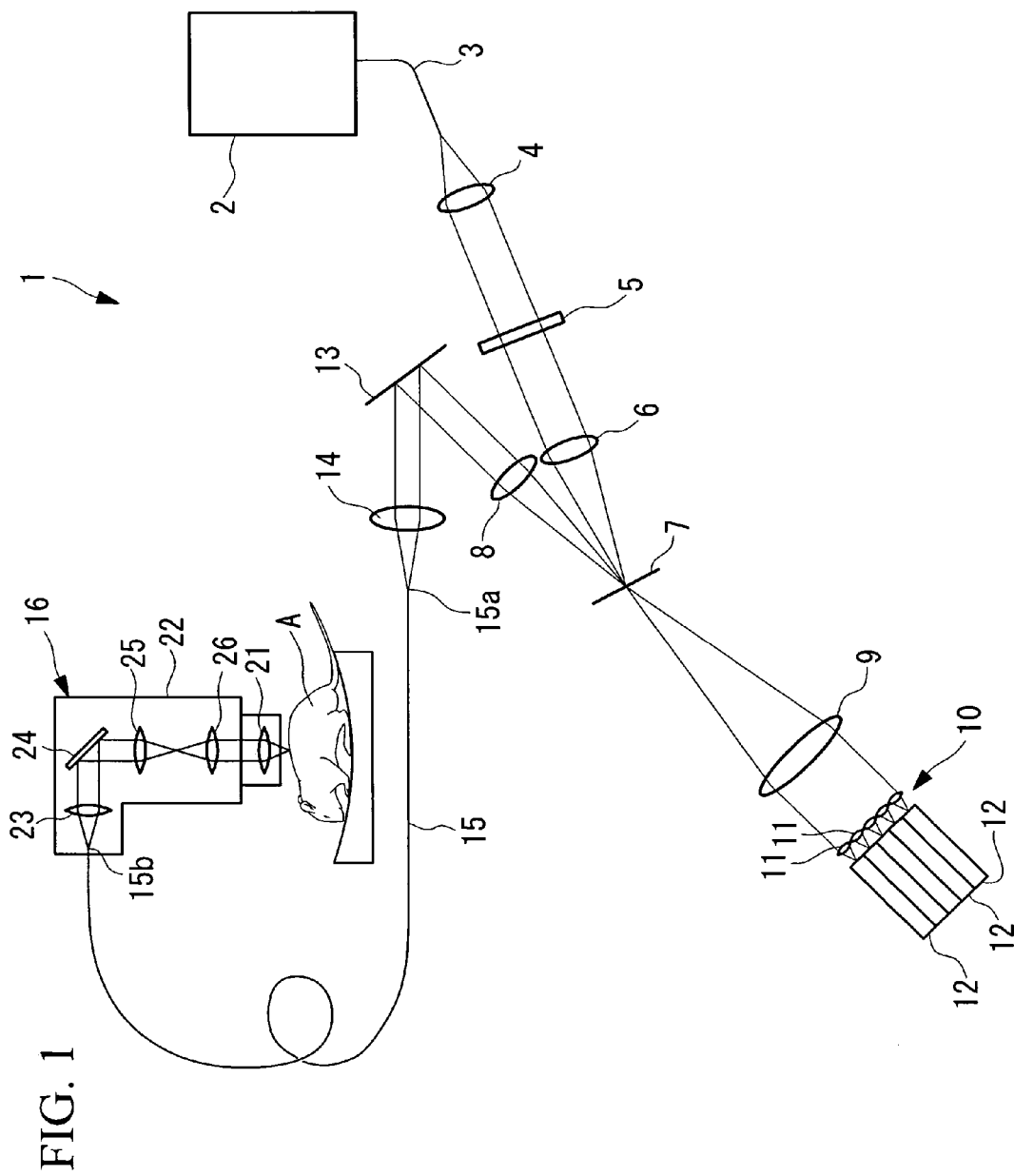
FIG. 1 is a schematic diagram depicting a laser-scanning fluoroscopy apparatus according to a first embodiment of the present invention.

Referring to FIG. 1, a laser-scanning fluoroscopy apparatus 1 according to this embodiment includes a laser combiner (laser light source) 2 emitting laser beams with a plurality of wavelengths; a first optical fiber 3 for guiding the laser beams from the laser combiner 2; a first collimator lens 4 for converting the laser beams emitted from an end surface of the first optical fiber 3 into collimated light; an acoustooptic element (spectroscopic device) 5 for splitting the laser beams with a plurality of wavelengths so that the laser beams are deflected in different directions according to wavelength; a first focusing lens 6 for focusing the plurality of laser beams emitted from the acoustooptic element 5 onto different focal positions arranged in a split direction; a wavelength-selecting reflection plate 7 arranged near a focal position of the first focusing lens 6; a second collimator lens 8 for converting the laser beams reflected at the wavelength-selecting reflection plate 7 into collimated light; a third collimator lens 9 arranged at a position opposite to the second collimator lens 8 on the other side of the above-described wavelength-selecting reflection plate 7; a lens array 10 for focusing the collimated light emitted from the third collimator lens 9; a plurality of photodetectors 12 arranged side by side in the split direction at the focal positions of lenses 11 constituting the lens array 10; a diffraction grating 13 for combining the laser beams emitted from the second collimator lens 8; a second focusing lens 14 for focusing the laser beams combined by the diffraction grating 13; a second optical fiber 15 having one end surface 15a thereof arranged near the focal position of the second focusing lens 14; and a measurement head 16 connected to the other end of the second optical fiber 15.

The laser combiner 2 combines a plurality of laser beams with different wavelengths from a plurality of laser oscillators (not shown in the figure) and outputs them. The laser oscillators oscillate laser beams with wavelengths of, for example, 400 nm, 488 nm, 543 nm, 633 nm, and 800 nm, respectively.

In response to a predetermined input frequency, the acoustooptic element 5 diffracts laser beams in different directions depending on the wavelengths. Thus, a plurality of laser beams with different wavelengths are split by the acoustooptic element 5 and are emitted in their respective predetermined directions. Furthermore, the input frequency to the acoustooptic element 5 can be finely adjusted, and thus, the emission direction of each laser beam can be finely adjusted.

Figure 2:
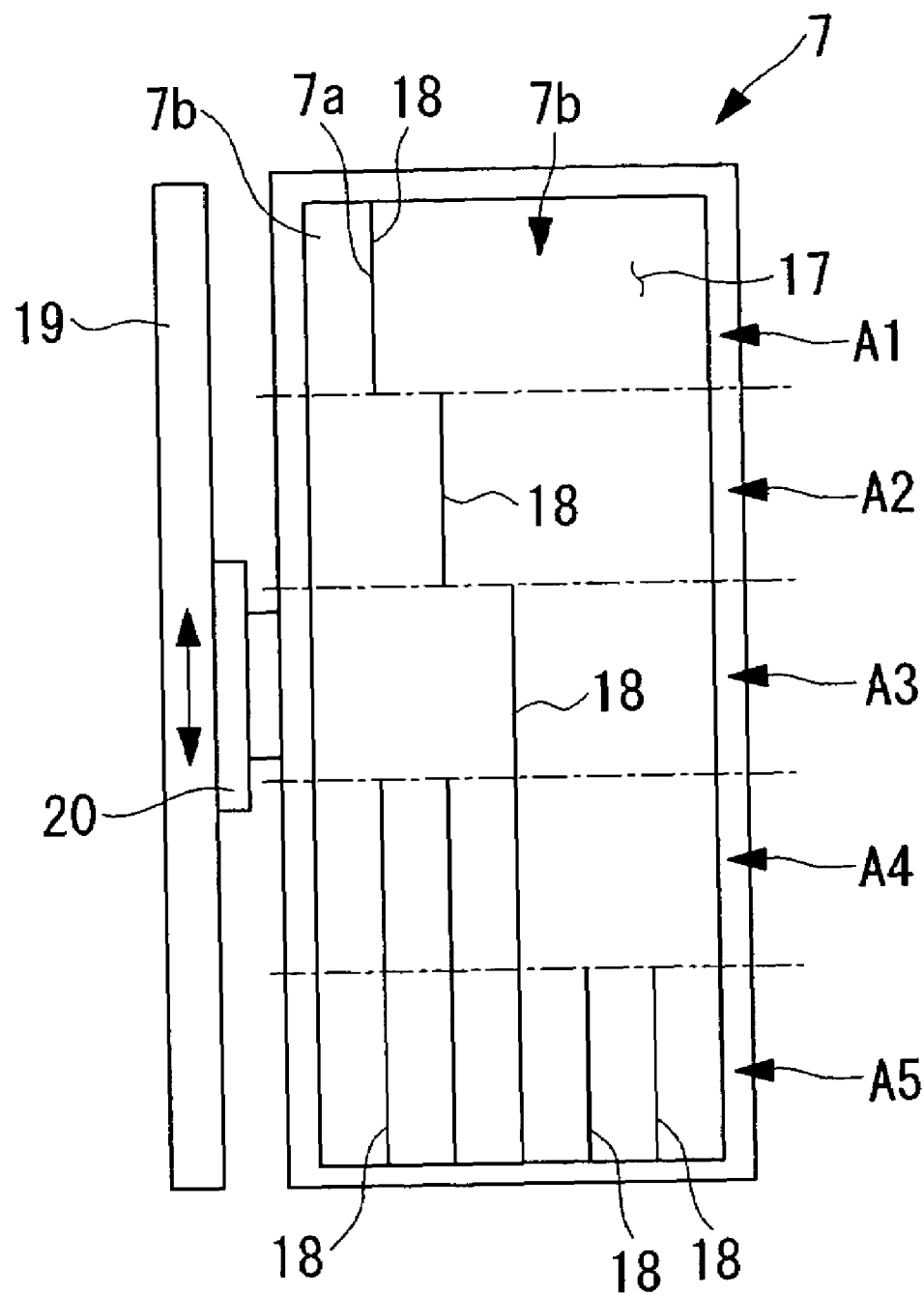
FIG. 2 is a front elevational view of a wavelength-selecting reflection plate in the laser-scanning fluoroscopy apparatus shown in FIG. 1.
Figure 3:
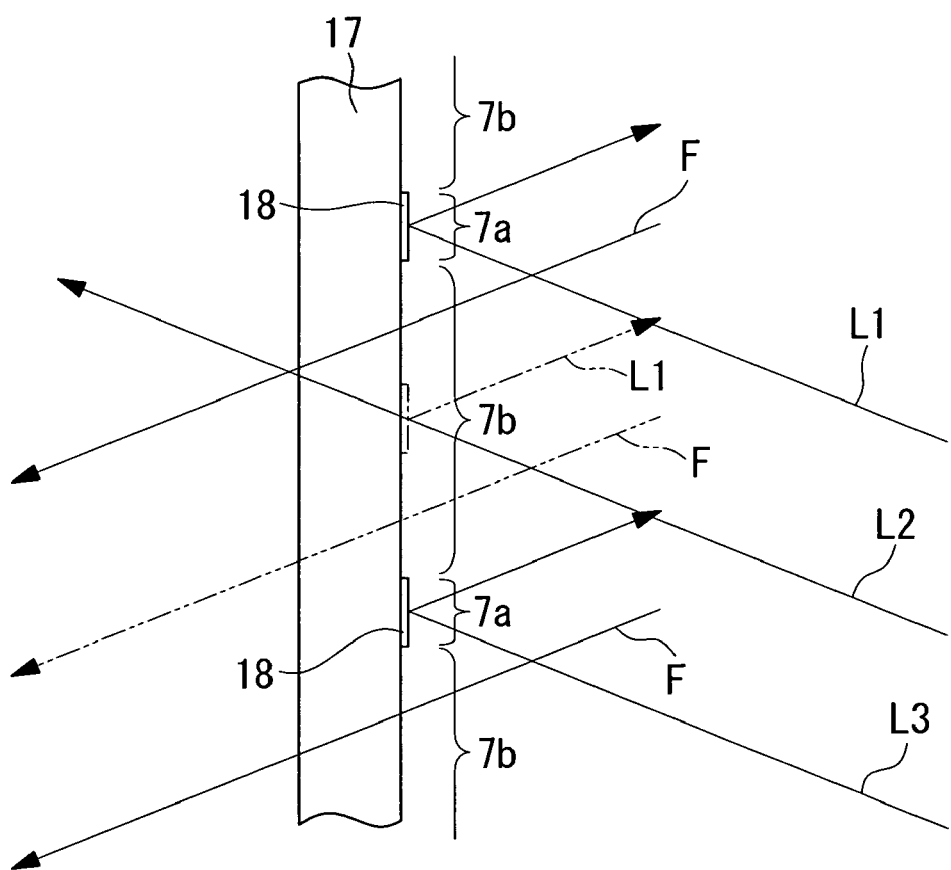
FIG. 3 is a schematic diagram illustrating transmission of a laser beam and reflection of fluorescence at the wavelength-selecting reflection plate shown in FIG. 2.

As shown in FIGS. 2 and 3, the wavelength-selecting reflection plate 7 is coated with strips of reflection films 18 extending in a longitudinal direction on one surface of a rectangular transparent substrate 17. Referring to FIG. 3, reflection sections 7a reflecting laser beams are provided at positions of the reflection films 18, whereas transmission sections 7b transmitting substantially 100% of light incident thereon are provided at the positions other than the positions of the reflection films 18.

Referring to FIG. 2, the wavelength-selecting reflection plate 7 is divided into five areas A1 to A5 arranged contiguously in the longitudinal direction. In the first area A1, the reflection film 18 is provided only at a position onto which a 400-nm laser beam is focused. In the second area A2, the reflection film 18 is provided only at a position onto which a 488-nm laser beam is focused. In the third area A3, the reflection film 18 is provided only at a position onto which a 543-nm laser beam is focused. Furthermore, in the fourth area A4, the reflection films 18 are provided at positions onto which 400-nm, 488-nm, and 543-nm laser beams are focused, respectively. In the fifth area A5, the reflection films 18 are provided at positions onto which 400-nm, 488-nm, 543-nm, 633-nm, and 800-nm laser beams are focused, respectively.

The width dimensions of the reflection sections 7a and the transmission sections 7b are proportional to the width of the spectral band of the light.

According to this embodiment, light with a spectral band of 400 to 800 nm can be split between the outermost reflection sections 7a. If a width dimension H1 between the outermost reflection sections 7 is 400, it is sufficient that the width dimension H2 of each reflection section 7a be 1 for an ideal laser beam. In this case, for example, in the area A5, the width dimension of the transmission section 7b arranged between the reflection section 7a for 400-nm light and the reflection section 7a for 488-nm light is 87; the width dimension of the transmission section 7b between the reflection sections 7a for 488-nm light and 543-nm light is 54; the width dimension of the transmission section 7b between the reflection sections 7a for 543-nm light and 633-nm light is 89; and the width dimension of the transmission section 7b between the reflection sections 7a for 633-nm light and 800-nm light is 166.

In the above-described case, the ratio of the width dimension H1 corresponding to the splittable spectral band 400 to 800 nm to the width dimension H2 of the reflection section 7a is 400:1. If a semiconductor laser is used as the laser light source, variations etc. in wavelength occur due to temperature changes, and hence it is preferable that the ratio between the width dimension H1 corresponding to the splittable spectral band and the width dimension H2 of each reflection section 7a be about 400:5. Furthermore, the size ratio H1:H2 should preferable be about 400:25 if assembly and adjustment work are to be facilitated.

In addition, the size of the apparatus can be reduced by reducing the spectral band of splittable light. If this is the case, the splittable spectral band may be about 100 nm, such as 500 to 600 nm. In this case, the size ratio H1:H2 is 100:25.

Therefore, it is preferable that conditional expression (1) shown below be satisfied:

$$100:25<H1:H2<400:1 \quad (1)$$

The wavelength-selecting reflection plate 7 is secured on a slider 20 that can be moved in a longitudinal direction by a linear guide 19. The slider 20 allows the position of the wavelength-selecting reflection plate 7 to be changed in the longitudinal direction by a linear-motion mechanism (not shown in the figure), such as a motor or a ball screw. In other words, a laser beam and fluorescence can be incident upon any one of the five areas A1 to A5 of the wavelength-selecting reflection plate 7.

As shown in FIG. 3, a laser beam L1 with a wavelength corresponding to a reflection film 18 arranged in the areas A1 to A5 in the light path is incident upon the position of the reflection film 18 and is reflected at that position. A laser beam L2 is discarded through a transmission section 7b, as indicated by dotted lines, because no reflection films 18 corresponding to its wavelength exist.

The photodetectors 12 are, for example, photomultiplier tubes (PMTs).

The diffraction grating 13 reflects one laser beam emitted through the second collimator lens 8 or combines and reflects a plurality of laser beams with different wavelengths, while splitting fluorescence F with at least one wavelength returning from a tissue A onto the second collimator lens 8.

The second optical fiber 15 is a single-mode fiber. An end surface 15b of the second optical fiber 15 has a conjugate positional relationship with the focal position of an objective lens 21 arranged at an end of the measurement head 16 to be described below.

The measurement head 16 includes, in a casing 22 having the objective lens 21 fixed at the end opposed to the tissue A, a fourth collimator lens 23 for converting light propagated through the second optical fiber 15 into collimated light; a scanning section 24 for two-dimensionally scanning the collimated light emitted from the fourth collimator lens 23; a pupil-projection lens 25 for focusing the laser beams scanned by the scanning section 24 to form an intermediate image; and an imaging lens 26 for focusing the laser beams of the intermediate image onto the objective lens 21.

The scanning section 24 includes so-called proximity galvano mirrors, which are, for example, two galvano mirrors supported so as to be rockable about mutually orthogonal axes.

The operation of the laser-scanning fluoroscopy apparatus 1 according to this embodiment, with the above-described structure, will now be described.

When fluoroscopy of only a laser beam with a wavelength of, for example, 400 nm is to be carried out using the laser-scanning fluoroscopy apparatus 1 according to this embodiment, the laser-scanning fluoroscopy apparatus 1 is configured such that the area A1 is positioned in the light path by operating the linear guide 19 to move the slider 20. A laser beam is emitted from the laser combiner 2. At this time, all laser oscillators may be turned ON to emit laser beams L1 and L2 including all wavelengths, or alternatively, only a corresponding laser oscillator for emitting the laser beam L1 with a wavelength of 400 nm may be turned ON.

When all laser oscillators are turned ON to emit the laser beams L1 and L2 including all wavelengths, the laser beams L1 and L2 are converted into collimated light by the collimator lens 4 and then enter the acoustooptic element 5. In the acoustooptic element 5, the laser beams L1 and L2 are split according to wavelength, each of the laser beams L1 and L2 becomes a strip of light with a single wavelength, and the laser beams L1 and L2 are emitted in different directions determined according to their respective wavelengths. Each of the emitted laser beams L1 and L2 is focused by the first focusing lens 6 and is incident upon the wavelength-selecting reflection plate 7 arranged near the focal position.

Since the area A1 of the wavelength-selecting reflection plate 7 is positioned in the light path, the reflection film 18 is provided only at the position corresponding to the focal position of a laser beam with a wavelength of 400 nm. Therefore, only the laser beam L1 with a wavelength of 400 nm is reflected at the reflection section 7a, and the laser beam L2 with another wavelength is discarded through the transmission section 7b. If the laser oscillators for the other wavelengths are turned OFF, only the laser beam L1 is reflected at the reflection section 7a.

The laser beam L1 with a wavelength of 400 nm reflected at the wavelength-selecting reflection plate 7 is converted into collimated light by the second collimator lens 8 and is then reflected at the diffraction grating 13. The laser beam L1, which has passed though the second collimator lens 8, includes a wavelength of 400 nm only and is reflected by the diffraction grating 13 at a predetermined deflection angle only towards the second focusing lens 14.

The laser beam L1 focused by the second focusing lens 14 is incident upon the end surface 15a of the second optical fiber 15 arranged at the focal position, and is transmitted to the measurement head 16 through the second optical fiber 15.

The laser beam L1 propagated through the second optical fiber 15 is converted into collimated light by the fourth collimator lens 23, scanned two-dimensionally by the scanning section 24, and radiated to the tissue A through the pupil-projection lens 25, the imaging lens 26, and the objective lens 21. The fluorescence F generated in the tissue A as a result of excitation by the laser beam L1 with a wavelength of 400 nm is focused onto the end surface 15b of the second optical fiber 15 through the objective lens 21, the imaging lens 26, the pupil-projection lens 25, the scanning section 24, and the fourth collimator lens 23.

Since the end surface 15b of the second optical fiber 15 is arranged at a position having a conjugate positional relationship with the focal position of the objective lens 21, the end surface 15b functions as a confocal pinhole. This means that only light returning from positions near the focal position of the objective lens 21 is incident upon the second optical fiber 15. As a result, only the fluorescence F coming from positions near the focal position of the objective lens 21 is detected by the photodetector 12. In this manner, a two-dimensional fluorescence image of the tissue A can be acquired at the focal position of the objective lens 21 formed at predetermined depths in the tissue A.

The fluorescence F returning through the second optical fiber 15 is converted into collimated light by the second focusing lens 14, is split through reflection at the diffraction grating 13, and is emitted in a direction determined according to the wavelength. The fluorescence F split according to the wavelength is focused by the second collimator lens 8 and is incident upon the wavelength-selecting reflection plate 7. Since the fluorescence F has a wavelength close to but different from that of the laser beam L1 (i.e., a wavelength of 400 nm in this example), the fluorescence F is incident upon a different position from that of the laser beam L1 on the wavelength-selecting reflection plate 7.

If the laser beam L1 with a wavelength of 400 nm is included in the return light from the measurement head 16, the laser beam L1 returns along the same light path and is reflected by the diffraction grating 13 in the original direction from which the laser beam L1 has come. Therefore, the laser beam L1 is incident upon the position corresponding to the reflection film 18 of the wavelength-selecting reflection plate 7, and thereby is reflected at (i.e., does not pass through) the wavelength-selecting reflection plate 7. On the other hand, since the fluorescence F in the return light has a wavelength different from the wavelength 400 nm, it is incident upon a different position from that of the reflection film 18 on the wavelength-selecting reflection plate 7. In an area neighboring the reflection section 7a composed of the reflection film 18, a transmission section 7b sufficiently wider than the reflection film 18 is provided. This transmission section 7b is subjected to anti-reflection processing to transmit about 100%, namely, almost all of the fluorescence F incident upon the wavelength-selecting reflection plate 7. The transmitted fluorescence F, which has passed through the wavelength-selecting reflection plate 7, is converted into collimated light by the third collimator lens 9 and enters the photodetectors 12 for respective wavelengths through the lens array 10.

Furthermore, when the laser beam L1 with a wavelength of 488 nm or 543 nm is to be radiated onto the tissue A for fluoroscopy, when the laser beams L1 with three different wavelengths of 400 nm, 488 nm, and 543 nm are to be simultaneously radiated onto the tissue A for fluoroscopy, and when the laser beams L1 with five different wavelengths of 400 nm, 488 nm, 543 nm, 633 nm, and 800 nm are to be simultaneously radiated onto the tissue A for fluoroscopy, the linear guide 19 is operated to move the slider 20 in the longitudinal direction of the wavelength-selecting reflection plate 7. In this manner, an appropriate one of the areas A2 to A5 of the wavelength-selecting reflection plate 7 is positioned in the light path.

As a result, from among the laser beams L1 and L2 incident upon the areas A2 to A5, only the laser beams L1 for which reflection films 18 exist at positions corresponding to the wavelengths are reflected by the reflection films 18 and radiated onto the tissue A. The fluorescence F returning from the tissue A passes through a transmission section 7b of the wavelength-selecting reflection plate 7 and is detected by the corresponding photodetector 12.

As described above, with the laser-scanning fluoroscopy apparatus 1 according to this embodiment, the spectral bands of the laser beams L1 and L2 oscillated by the respective laser oscillators can be limited to a narrow spectral band by employing the laser combiner 2. Therefore, the laser beams L1 and L2, after having been split by the acoustooptic element 5, can be formed as long, thin strips of light, so that the laser beams L1 with a plurality of wavelengths can be reflected by the respective strips of reflection films 18. On the other hand, the transmission section 7b in a wide area neighboring the reflection film 18 allows all fluorescence F with spectral bands neighboring the wavelengths of the laser beams L1 to be efficiently transmitted for collection by the photodetectors 12.

As a result, the fluorescence F can be separated from the laser beams L1 without using a dichroic mirror. Furthermore, even in a case where the Stokes' shift is too small to separate the fluorescence F with a dichroic mirror, the fluorescence F can be separated from the laser beams L1 more reliably.

In the laser-scanning fluoroscopy apparatus 1 according to this embodiment, the measurement head 16 is connected to the second optical fiber 15 to freely arrange the measurement head 16 in any orientation by bending the second optical fiber 15. Therefore, the laser-scanning fluoroscopy apparatus 1 according to this embodiment is suitable for applications where the observer wishes to bring the objective lens 21 towards the tissue A from various directions or the observer wishes to allow the tissue A, such as a small laboratory animal, to move freely while having the objective lens mounted thereon for the purpose of examining the tissue A in vivo.

Figure 4:
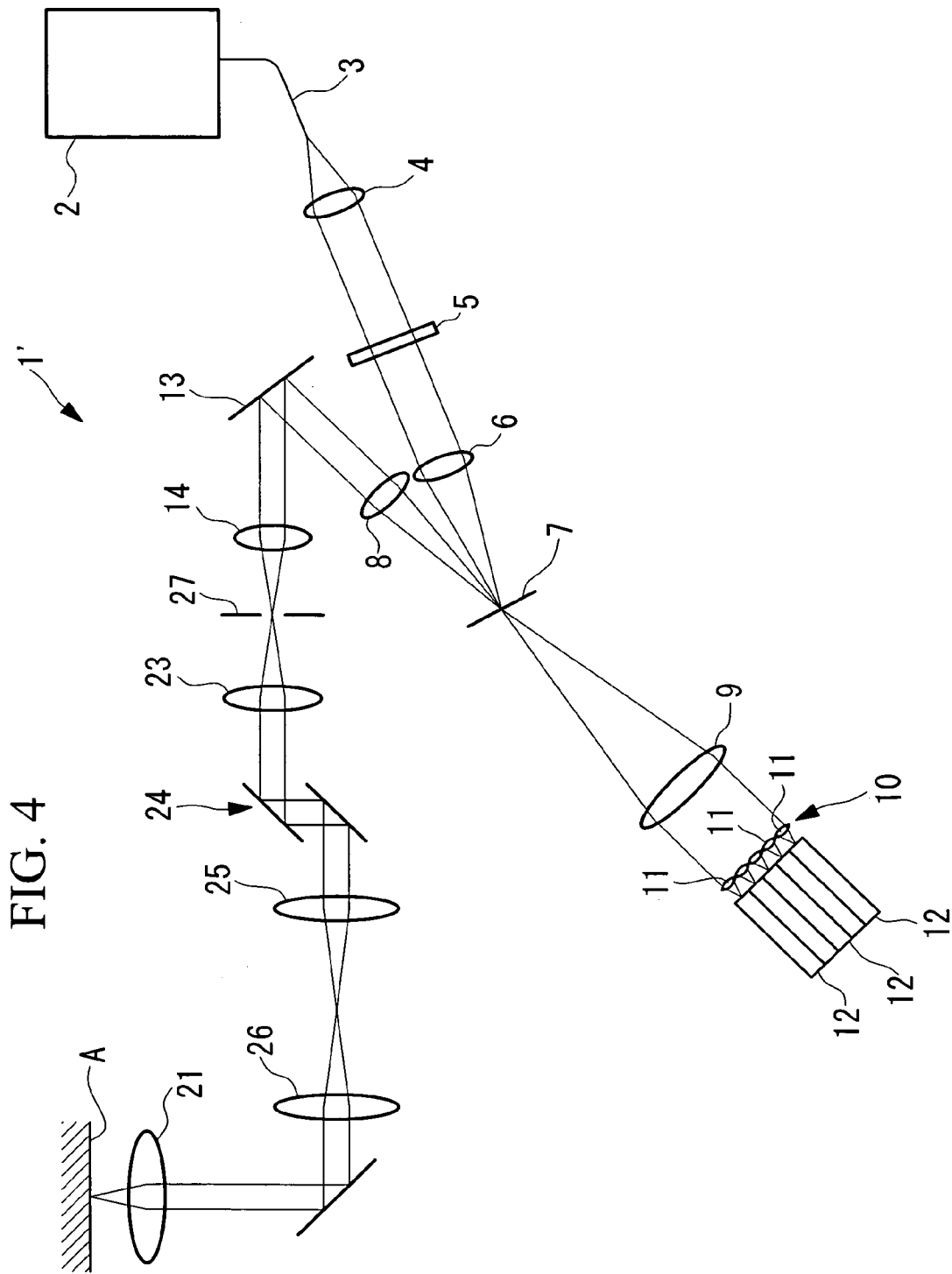
FIG. 4 is a schematic diagram depicting a modification of the laser-scanning fluoroscopy apparatus shown in FIG. 1.

Alternatively, as shown in FIG. 4, a laser-scanning fluoroscopy apparatus 1' where the objective lens 21 is fixed by removing the second optical fiber 15 may be employed. In this case, it is preferable that a confocal aperture 27 be arranged near the focal position of the second focusing lens 14 in place of the second optical fiber 15. In this manner, the same advantages can be achieved by directly replacing the confocal aperture function offered by the end surface 15b of the second optical fiber 15 with the confocal aperture 27.

Figure 5:
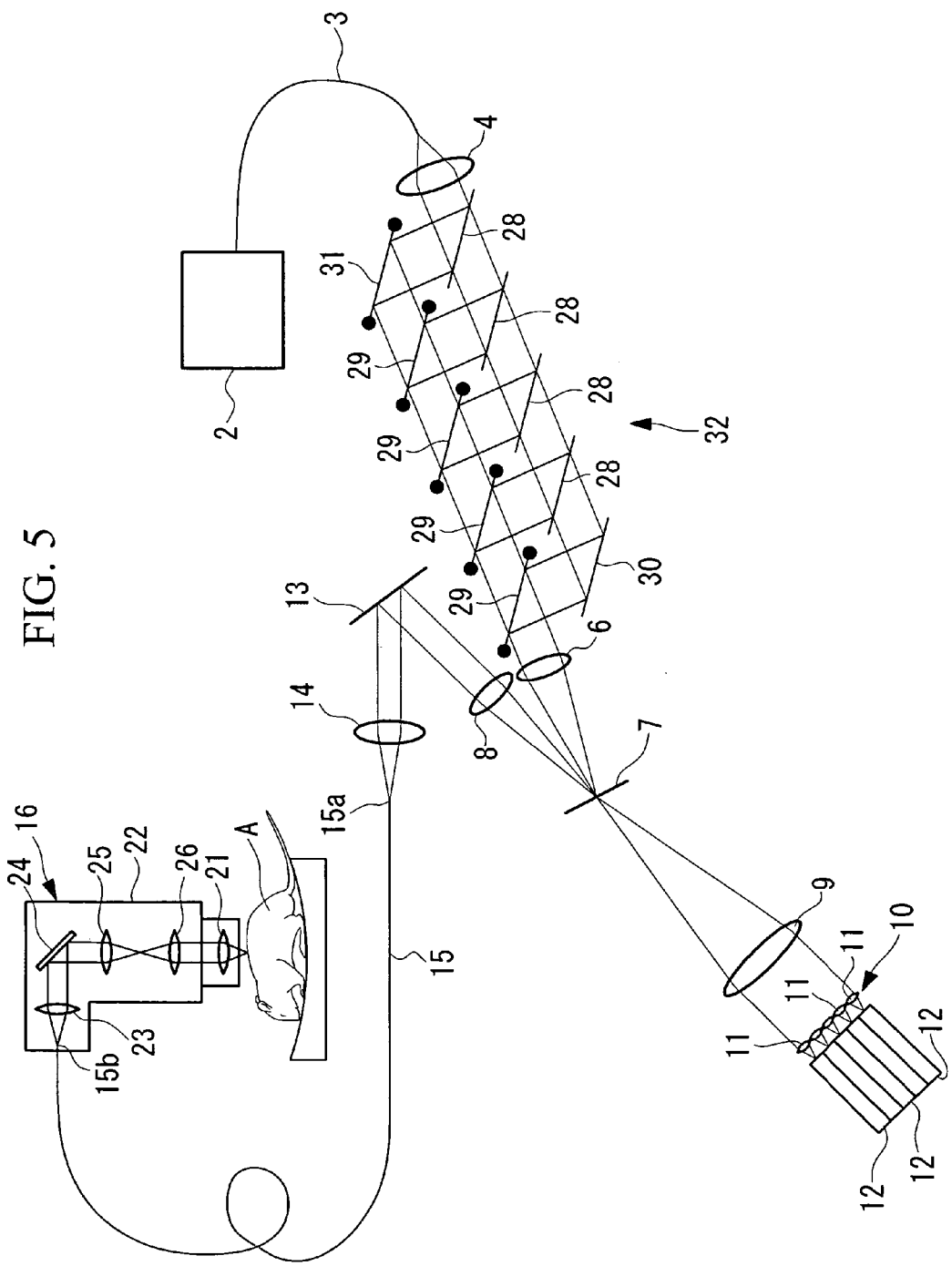
FIG. 5 is a schematic diagram depicting another modification of the laser-scanning fluoroscopy apparatus shown in FIG. 1.
Figure 6:
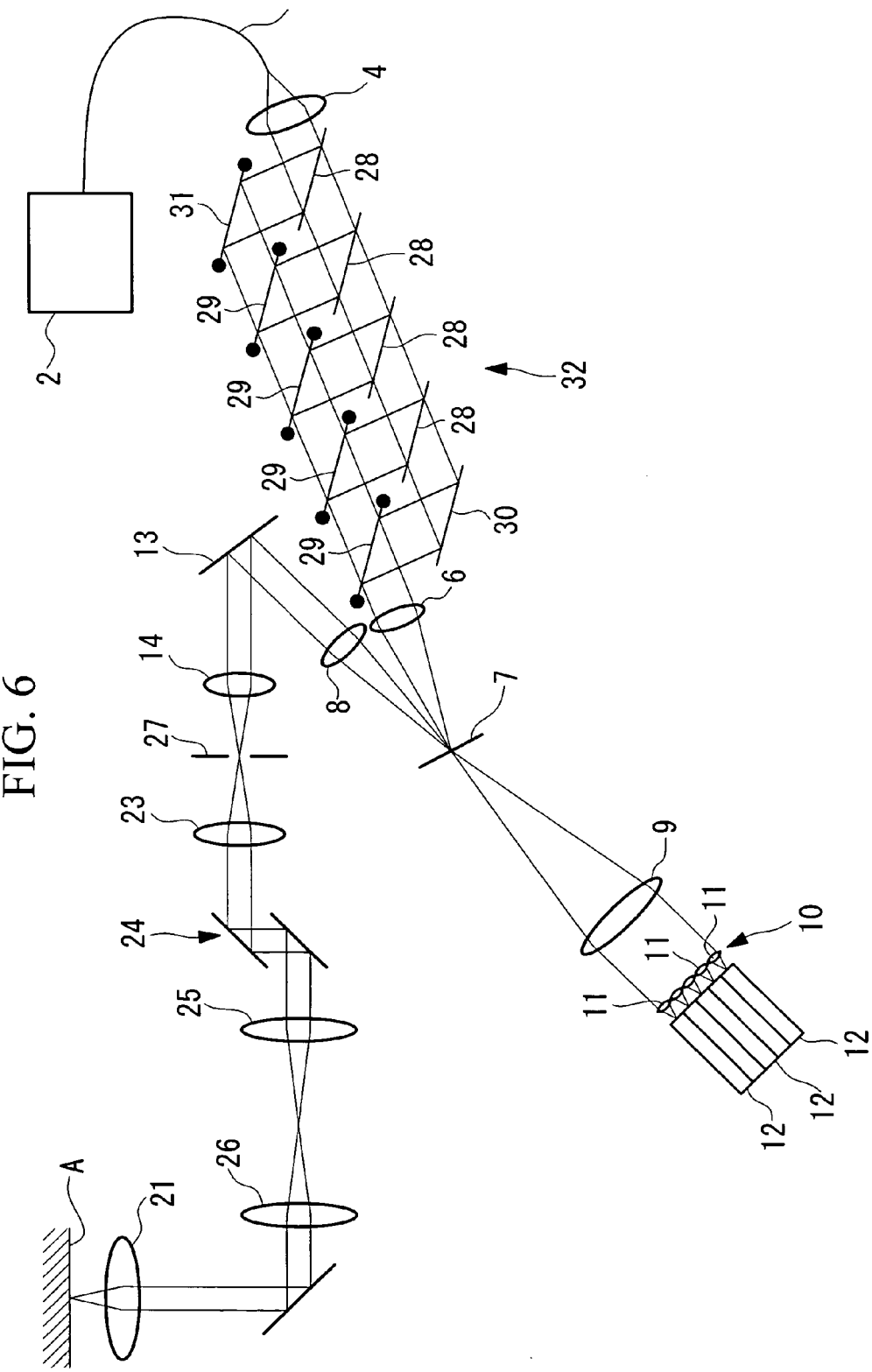
FIG. 6 is a schematic diagram depicting still another modification of the laser-scanning fluoroscopy apparatus shown in FIG. 1.

The above-described embodiment has been described by way of the acoustooptic element 5 as a spectroscopic device for splitting a beam including the laser beams L1 and L2 with a plurality of wavelengths emitted from the laser combiner 2 into the laser beams L1 and L2 according to their respective wavelengths. Instead, as shown in FIGS. 5 and 6, a spectroscopic device 32 including a plurality of dichroic mirrors 28 and 29 and mirrors 30 and 31, which are combined, may be adopted. In this case, the focal positions of the laser beams L1 and L2 with different wavelengths through the first focusing lens 6 can be finely adjusted in a split direction by finely adjusting the angle of each dichroic mirror 29. FIG. 5 is a schematic diagram depicting a modification of the laser-scanning fluoroscopy apparatus 1 according to the first embodiment shown in FIG. 1, where the second optical fiber 15 is employed. FIG. 6 is a schematic diagram depicting a modification of the laser-scanning fluoroscopy apparatus 1 according to the first embodiment shown in FIG. 4, where the second optical fiber 15 is not employed.

Furthermore, the spectroscopic device to be employed is not limited to the acoustooptic element 5 or the spectroscopic device 32, where the dichroic mirrors 28 and 29 etc. are included. Alternatively, any spectroscopic device including a prism can be employed.

A laser-scanning fluoroscopy apparatus 40 according to a second embodiment of the present invention will now be described with reference to FIGS. 7 to 9.

The same components in this embodiment as those used in the laser-scanning fluoroscopy apparatuses 1 and 1' according to the first embodiment are denoted by the same reference numerals, and thus will not be described.

Figure 7:
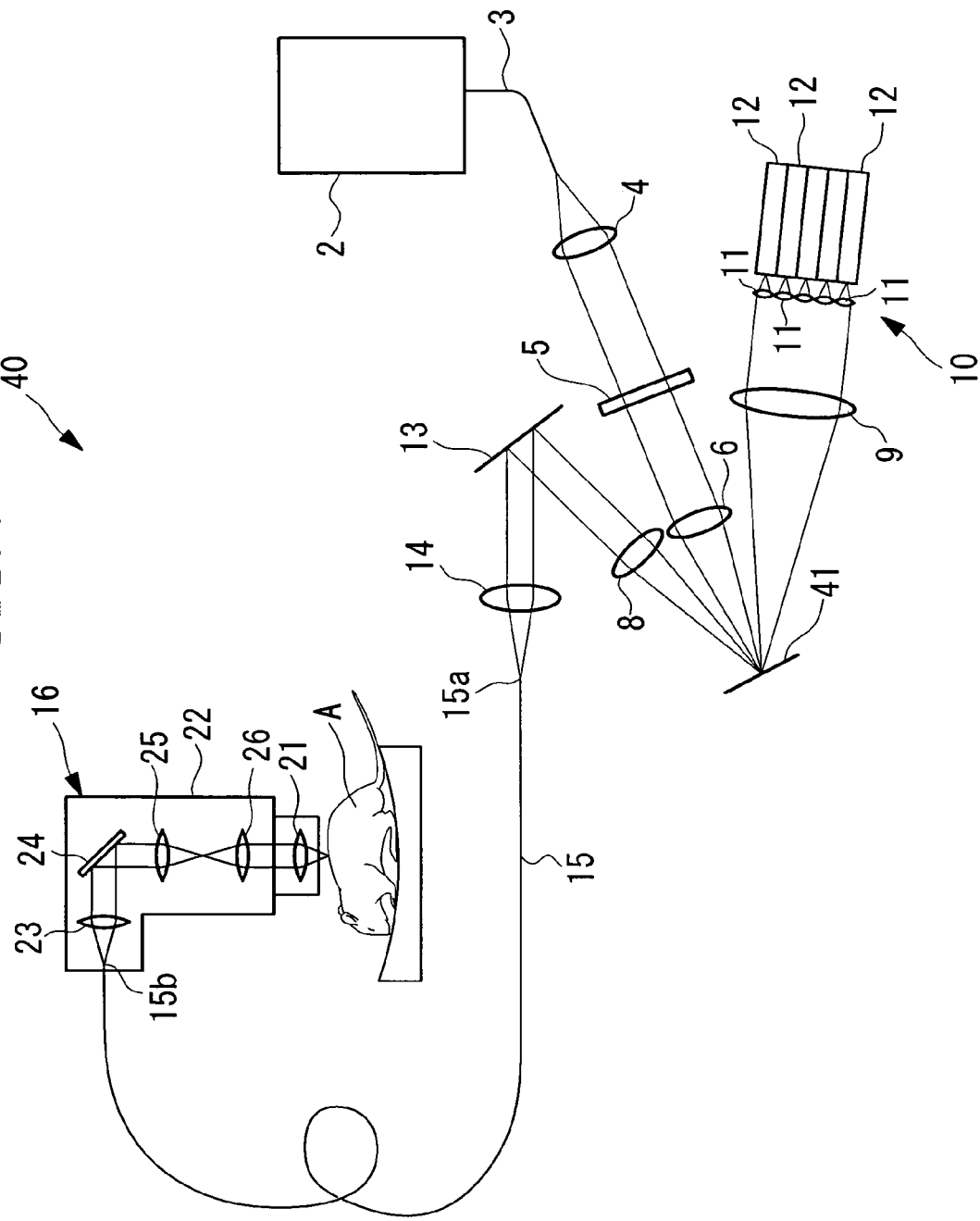
FIG. 7 is a schematic diagram depicting a laser-scanning fluoroscopy apparatus according to a second embodiment of the present invention.

Referring to FIG. 7, the laser-scanning fluoroscopy apparatus 40 according to this embodiment includes a mirror array 41 including a plurality of micro-mirrors in place of the wavelength-selecting reflection plate 7 included in the laser-scanning fluoroscopy apparatus 1 according to the first embodiment.

Figure 8:
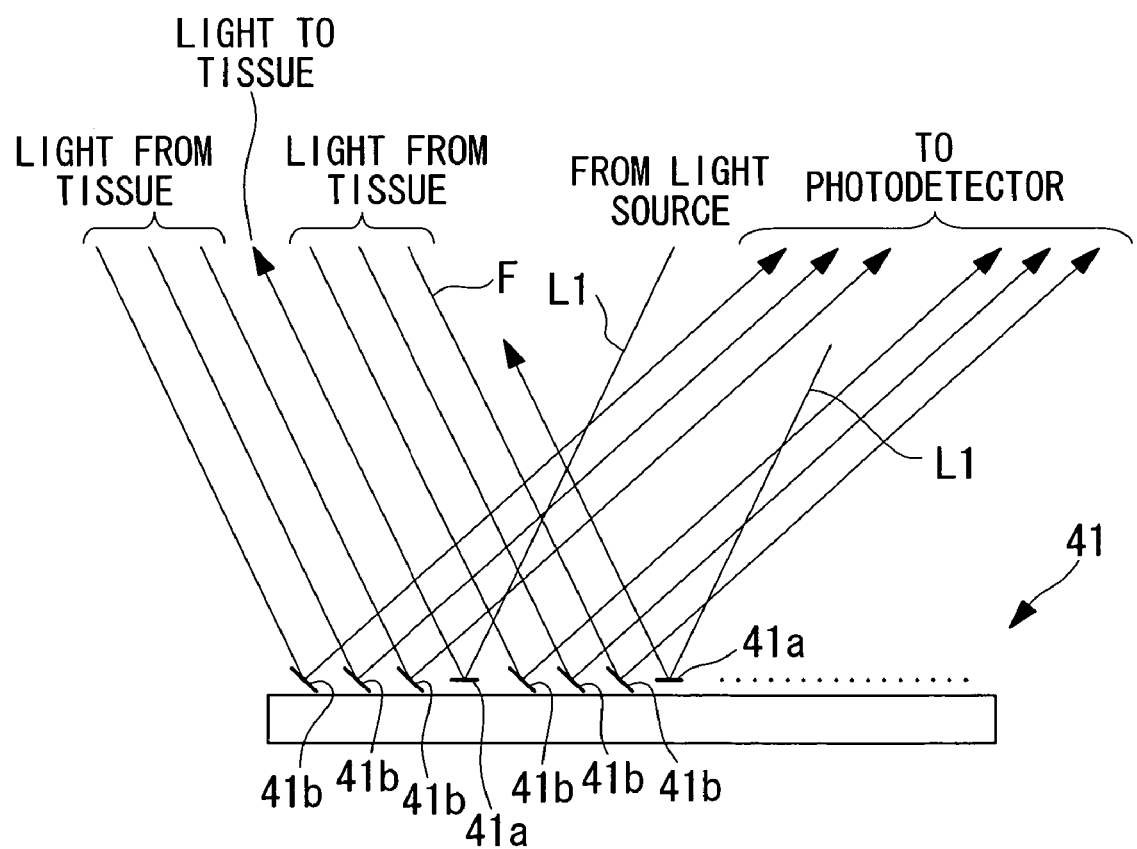
FIG. 8 is a schematic diagram illustrating reflection of a laser beam and fluorescence at a mirror array of the laser-scanning fluoroscopy apparatus shown in FIG. 7.

As shown in FIG. 8, the mirror array 41 includes first mirrors 41a disposed in the form of linear strips at a first reflection angle at the same positions as the reflection sections 7a on the wavelength-selecting reflection plate 7 in the laser-scanning fluoroscopy apparatus 1 according to the first embodiment; and second mirrors 41b fixed at a second reflection angle at the same positions as the transmission sections 7b. The mirror array 41 further includes the same areas A1 to A5 (not shown in the figure) as those arranged along the longitudinal direction of the wavelength-selecting reflection plate 7 according to the first embodiment. These mirrors 41a and 41b extend over each of the areas.

The first mirrors 41a are arranged at the focal positions onto which the laser beams L1 with wavelengths are focused by the first focusing lens 6. The first reflection angle is set so that the laser beams L1 sent from the laser light source 2 are reflected towards the second collimator lens 8. On the other hand, the second mirrors 41b are arranged at positions on which the fluorescence F returning from the second collimator lens 8 is incident. The second reflection angle is set so that the fluorescence F is reflected towards the photodetectors 12 arranged in a direction different from that of the first focusing lens 6.

Although the second mirrors 41b have the same width dimensions as the first mirrors 41a, the width dimension of each first mirror 41a along the split direction is set sufficiently small compared with the total width dimension of a set of second mirrors 41b by arranging the set of second mirrors 41b between two first mirrors 41a. The first mirrors 41a only need to reflect the incident laser beams L1 having a limited spectral band. On the other hand, the fluorescence F, having a relatively wide spectral band neighboring the wavelengths of the laser beams L1, which is generated by the tissue A irradiated with the same laser beams L1, needs to be guided to the second mirrors 41b.

Furthermore, if the wavelengths of the laser beams L1 to be radiated onto the tissue A are to be changed, the linear guide 19 is operated to move the mirror array 41 along its longitudinal direction, so that the areas A1 to A5 to be positioned in the light path can be changed.

As described above, the laser-scanning fluoroscopy apparatus 40 according to this embodiment can also offer the same advantages as those of the laser-scanning fluoroscopy apparatus 1 according to the first embodiment in that the laser-scanning fluoroscopy apparatus 40 can split the fluorescence F from the laser beams L1 for efficient detection without using a dichroic mirror.

Figure 9A:
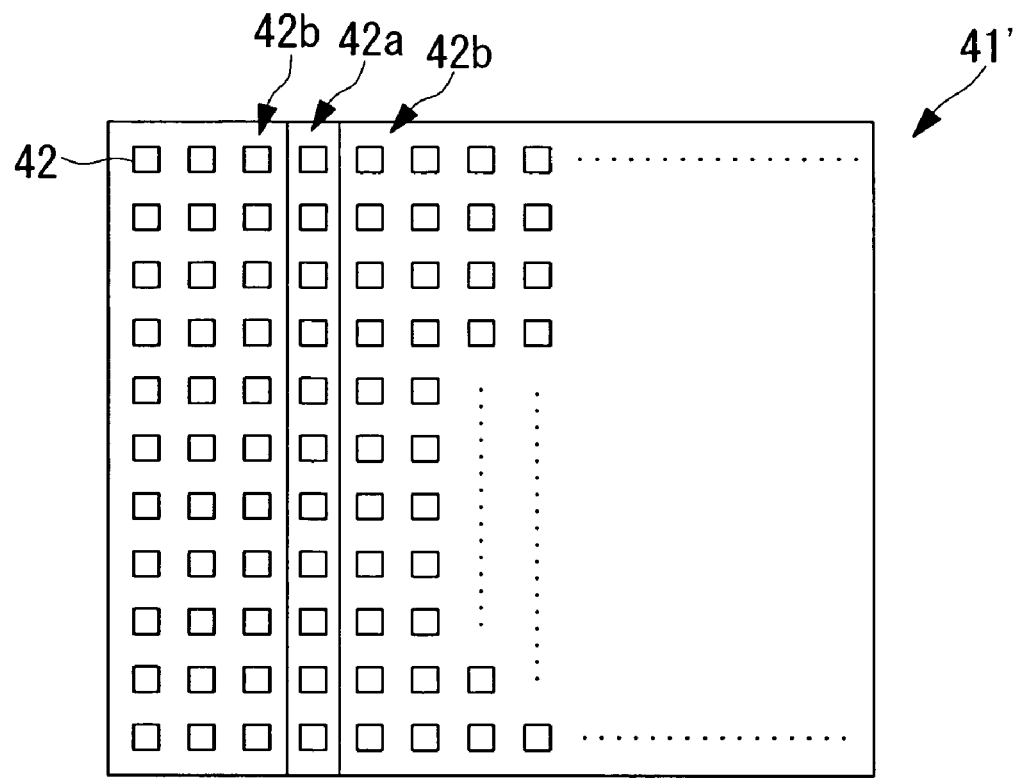
FIG. 9A is a plan view of a modification of the mirror array shown in FIG. 8.
Figure 9B:
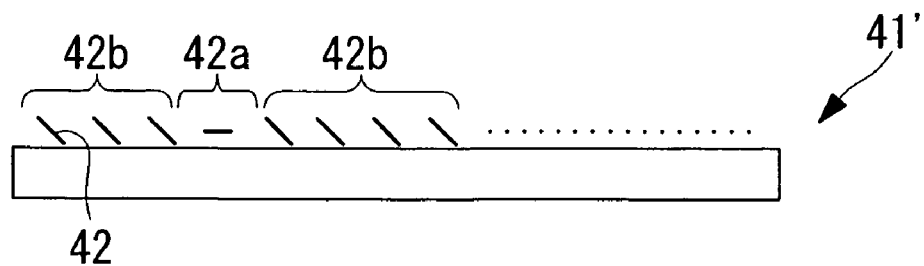
FIG. 9B is a front view of the modification of the mirror array shown in FIG. 8.

In the above-described embodiment, the mirror array 41 including the first mirrors 41a and the second mirrors 41b fixed at different reflection angles are adopted, and the mirror array 41 is moved with the linear guide 19 in the longitudinal direction when the laser beams L1 radiated onto the tissue A are to be changed. Alternatively, as shown in FIGS. 9A and 9B, a scanning mirror element such as a digital micro-mirror device (DMD) having a plurality of movable micro-mirrors 42 arranged in an array may be adopted as a mirror array 41'.

In this case, the first reflection sections 42a and the second reflection sections 42 are constructed so as to form the same pattern as the reflection sections 7a and the transmission sections 7b of the wavelength-selecting reflection plate 7 according to the first embodiment, depending on the wavelengths of the laser beams L1 to be radiated onto the tissue A. Furthermore, the reflection sections 42a and 42b have different reflection angles, as required, when the pattern of the reflection sections 7a and the transmission sections 7b is to be changed, so that the laser beams L1 with a plurality of wavelengths are simultaneously radiated onto the tissue A and the fluorescence F with a plurality of wavelengths generated by the tissue A can be efficiently detected by the photodetectors 12.

Figure 10:
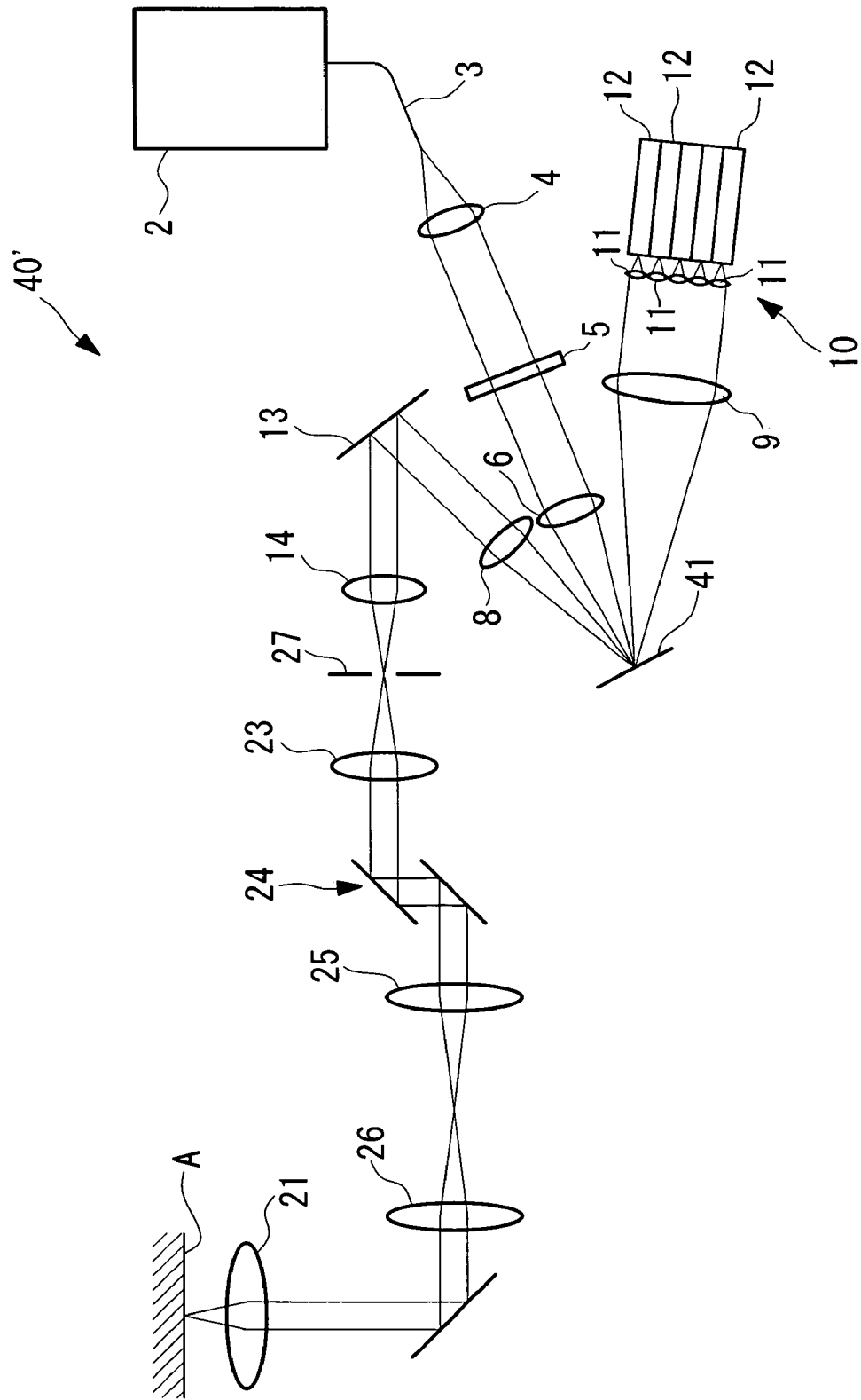
FIG. 10 is a schematic diagram depicting a modification of the laser-scanning fluoroscopy apparatus shown in FIG. 7.

As shown in FIG. 10, a structure without the second optical fiber 15 may also be adopted.

What is claimed is:

1. A laser-scanning fluoroscopy apparatus comprising:
   a laser light source for emitting laser beams with a plurality of wavelengths;
   a spectroscopic device for splitting the laser beams emitted from the laser light source according to wavelength;
   a focusing lens for focusing the laser beams split by the spectroscopic device;
   a mirror device including:
      a plurality of first reflection sections, disposed near focal positions of the focusing lens, spaced out in a split direction of the spectroscopic device to reflect the laser beams with different wavelengths in a first direction; and
      a second reflection section arranged adjacent to the first reflection sections to reflect incident light in a second reflection direction;
   a diffraction grating for combining the laser beams reflected by the first reflection sections in the first direction;
   a scanning section for two-dimensionally scanning the laser beams combined by the diffraction grating;
   an objective optical system for focusing the laser beams scanned by the scanning section onto a tissue; and
   a photodetector for detecting fluorescence emitted from the tissue, the fluorescence returning through the objective optical system, the scanning section, and the diffraction grating, and being reflected at the second reflection section of the mirror device, wherein
   a width dimension, as measured along the split direction, of each first reflection section of the mirror device is smaller than the width dimension of the second reflection section.

2. The laser-scanning fluoroscopy apparatus according to claim 1, wherein the mirror device includes a plurality of movable mirrors such that the first reflection sections and the second reflection section can be relocated.

* * * * *